United States Patent
McMains et al.

(10) Patent No.: US 6,579,905 B1
(45) Date of Patent: Jun. 17, 2003

(54) METHOD FOR THE PREVENTION OR TREATMENT OF HYPOMAGNESEMIA IN PEDIATRIC PATIENTS AND IN PATIENTS WITH G-TUBES OR NG-TUBES

(76) Inventors: Michael B. McMains, 20 N. Meridian St. Suite 9000, Indianapolis, IN (US) 46204; Caren D Geppert, 20 N. Meridian St. Suite 9000, Indianapolis, IN (US) 46204; Missy L. Siegel, 20 N. Meridian St. Suite 9000, Indianapolis, IN (US) 46204

( * ) Notice: Subject to any disclaimer, the term of this patent is extended or adjusted under 35 U.S.C. 154(b) by 0 days.

(21) Appl. No.: 09/988,104

(22) Filed: Nov. 19, 2001

(51) Int. Cl.$^7$ .............................................. A61K 31/195
(52) U.S. Cl. ....................................................... 514/561
(58) Field of Search ......................................... 514/561

(56) References Cited

U.S. PATENT DOCUMENTS

| | | |
|---|---|---|
| 4,041,154 A | 8/1977 | Helbig et al. |
| 4,104,370 A | 8/1978 | Bloch |
| 4,137,326 A | 1/1979 | Fischer et al. |
| 4,855,289 A | 8/1989 | Wester et al. |
| 4,954,349 A | 9/1990 | Sheth et al. |
| 5,143,732 A * | 9/1992 | Helbig et al. ............... 424/647 |
| RE34,222 E | 4/1993 | Bloch |
| 5,501,859 A | 3/1996 | Woods, Jr. et al. |
| 6,218,192 B1 * | 4/2001 | Altura et al. ................. 436/79 |

OTHER PUBLICATIONS

J. Dulach, et al., Magnesium and Therapeutics, Magnesium Research, 1994, 313–328, 7, 3/4.

G. Weiss, et al., Magnesium Aspartate Hydrochloride, New Cardiovascular Drugs, 1986, 243–257, Raven Press, New York.

J.K. Rude, Clinical Review: Magnesium Deficiency: A cause of heterogenous disease in humans. Journal of Bone and Mineral Research, 1998, 749–58, 13(40).

B. Muhlbauer, et al., Magnesium–L–aspartate HCL and magnesium oxide: bioavailability in healthy volunteers. European Journal of Clinical Pharmacology, 1991, 437–38, 40.

The Merck Manual of Diagnosis and Therapy, 14th ed., published by Merck & Co., Inc. (NJ), 1982, 942–44.

* cited by examiner

*Primary Examiner*—Raymond Henley, III

(57) ABSTRACT

A method of preventing or treating hypomagnesemia in pediatric patients and patients with G-tubes or NG-tubes comprising the step of administering a pharmaceutical composition comprised of a magnesium salt, magnesium-L-aspartate hydrochloride, in a water-soluble powder concentrate. When dissolved in water, the pharmaceutical composition provides a method for preventing or treating hypomagnesemia in such patients without compromising the absorption or efficacy of the pharmaceutical composition.

2 Claims, No Drawings

METHOD FOR THE PREVENTION OR TREATMENT OF HYPOMAGNESEMIA IN PEDIATRIC PATIENTS AND IN PATIENTS WITH G-TUBES OR NG-TUBES

BACKGROUND OF THE INVENTION

The present invention relates generally to the prevention or treatment of hypomagnesemia in pediatric patients and in patients with gastric tubes (G-tubes) or nasogastric tubes (NG-tubes). More particularly, the present invention relates to the administration of a powder concentrate magnesium supplement via a G-tube or NG-tube to patients in need thereof. The present invention also allows for the easy administration of a magnesium supplement to pediatric patients in need thereof.

Magnesium is essential for all living organisms and is required for over 300 different metabolic processes. For example, magnesium helps regulate the release of insulin by facilitating the activation of a tyrosine protein kinase receptor. In hypomagnesemic patients, the ability of insulin to activate the protein kinase receptor is impaired, which results in reduced peripheral glucose uptake. In addition, magnesium is a calcium antagonist and displaces calcium from cellular membrane receptors and enzymatic binding sites. One such example is the competition between calcium and magnesium for binding sites of troponin C, which is involved in muscle contractions. When magnesium binds to this receptor, it effectuates a smaller conformational change than if calcium binds to the receptor. Finally, one the mechanisms responsible for cardiac muscle contraction is the sodium/potassium pump. The driving force of this pump is a magnesium-dependant ATPase, which splits ATP. This in turn provides the energy needed for active ion transport. These are only a few of the many examples of magnesium's role in the human body.

Due to its involvement in so many cellular processes, magnesium deficiency has been shown to be associated with several disease states, including Type I and Type II diabetes, hypertension, cerebral and myocardial infarctions, atheroschlerosis, osteoporosis, PMS (headaches, fluid retention and mood changes), muscle cramps, and bipolar disorder. Furthermore, many prescription medications deplete the body of magnesium. These include, but are not limited to: loop diuretics, Thiazide diuretics, Corticosteroids, Glycosides and Estrogens and Estrogen derivatives.

Patients taking magnesium-depleting medications are often advised to supplement with oral magnesium. Magnesium supplementation is difficult because the current magnesium formulations on the market have low bioavailability and are not readily absorbed. Furthermore, these supplements often cause diarrhea.

One of the biggest problems, however, is the supplementation of pediatric patients, who are unable to swallow tablets, and patients with G-tubes or NG-tubes who are unable to take medication orally. Presently, health care providers must pulverize magnesium tablets to supplement pediatric patients and patients with G-tubes or NG-tubes. Not only is this process time consuming but it also compromises the absorption and efficacy of the product.

Therefore, a need exists for an improved composition and method for the prevention and treatment of hypomagnesemia in pediatric patients and patients with G-tubes and NG-tubes.

SUMMARY OF THE INVENTION

The present invention provides an improved method for the prophylaxis and treatment of hypomagnesemia in pediatric patients and in patients with G-tubes and NG-tubes. Particularly, the present invention provides an absorbable and bioavailable form of magnesium that can be effectively administered to pediatric patients and patients with G-tubes or NG-tubes in order to raise the blood levels of magnesium in such patients.

DETAILED DESCRIPTION

The present invention provides a method for increasing the blood magnesium levels in pediatric patients and patients with G-tubes or NG-tubes by administering a magnesium salt in the form of a hygroscopic powder to patients in need thereof. Preferably, the magnesium salt is magnesium-L-aspartate hydrochloride.

As stated above, there is presently no satisfactory method for the enteral administration of magnesium to patients with G-tubes or NG-tubes. In addition, there is no satisfactory method for the administration of magnesium to pediatric patients, who are unable to swallow tablets. Furthermore, existing magnesium formulations are poorly absorbed from the digestive tract. The present invention provides a readily bioavailable and absorbable magnesium salt in the form of a concentrated powder that can be dissolved in water and easily administered to pediatric patients or administered to patients via a G-tube or NG-tube.

The composition of the present invention includes a magnesium salt in the form of a water-soluble powder concentrate. In an embodiment, the magnesium salt is magnesium-L-aspartate hydrochloride. In said embodiment, magnesium-L-aspartate hydrochloride is in the form of granules and is comprised of, per dosing unit:

| Ingredient | Amount |
| --- | --- |
| Active Ingredient | |
| Magnesium-L-Aspartate HCl.3H$_2$O (equiv. to 121.53 mg of Mg) | 1230.0 mg |
| Excipients | |
| Sucrose | 4484.0 mg |
| Citric acid, anhydrous | 170.0 mg |
| Polyethylene glycol 6000 | 100.0 mg |
| Dry lemon flavoring essence | 16.0 mg |
| Total weight | 6000.0 mg |

The present invention also provides a method of raising magnesium blood levels in pediatric patients and patients with G-tubes or NG-tubes. The method includes the step of administering a bioavailable and absorbable magnesium composition having a magnesium salt in the form of a hygroscopic powder.

In an embodiment, the magnesium composition contains magnesium salt in an amount ranging from about 5 mEq to about 10 mEq.

In an embodiment, the magnesium composition is administered in a dosage ranging from about 122 mg/day to about 488 mg/day.

An advantage of the present invention is that it provides a bioavailable and absorbable form of magnesium that may be administered enterally to patients with G-tubes or NG-tubes or orally to pediatric patients. This granule formulation provides an inherent advantage over the traditional tablet form for these patients.

Another advantage is that the magnesium composition is acid-base neutral and does not interfere with the absorption of iron.

Still further, an advantage of the present invention is that it has no undesirable side effects.

What is claimed is:

1. A method of raising blood magnesium levels in a patient with a G-tube or NG-tube comprising administering a therapeutically effective amount of a readily bioavailable and absorbable magnesium salt in the form of a powder concentrate.

2. The method of claim 1, wherein said magnesium salt is magnesium-L-aspartate hydrochloride.

* * * * *